United States Patent [19]

Herkes

[11] Patent Number: 5,070,202

[45] Date of Patent: Dec. 3, 1991

[54] CYANOBUTYLATION OF AMINES WITH 2-PENTENITRILE

[75] Inventor: Frank E. Herkes, Wilmington, Del.

[73] Assignee: E. I. Du Pont de Nemours and Company, Wilmington, Del.

[21] Appl. No.: 500,572

[22] Filed: Mar. 28, 1990

[51] Int. Cl.$^5$ .................. C07D 295/00; C07D 211/26; C07C 255/00
[52] U.S. Cl. .................................... 544/402; 558/430; 558/435; 558/452; 558/453; 546/246
[58] Field of Search ............... 544/402, 382; 558/430, 558/435, 452, 453; 546/246

[56] References Cited

U.S. PATENT DOCUMENTS 4,211,725  7/1980  Kluger et al. ................. 558/452
4,496,474  1/1985  Reck ............................. 252/311.5

OTHER PUBLICATIONS

Kluger et al., Chem. Abst. 93-205630x (1980).
Reck, Chem. Abst. 101-156623v (1984).

*Primary Examiner*—Cecilia Shen

[57] ABSTRACT

A process for the production of alkylaminonitriles by reacting 2-pentenenitrile and an alkylamine in the presence of 15 to 60% by weight water.

6 Claims, No Drawings

CYANOBUTYLATION OF AMINES WITH 2-PENTENITRILE

FIELD OF THE INVENTION

This invention relates to an improved process for the reaction of 2-pentenenitrile with amines to produce alkylaminonitriles and bis-(3-alkylamino)dinitriles.

BACKGROUND OF THE INVENTION

U.S. Pat. No. 4,260,556 and U.S. Pat. No. 4,211,725 discloses the reaction of 2-pentenenitrile and "nucleophilic agents" such as ammonia and ethylenediamine to produce alkylaminonitriles and dimers. The reaction takes place in the presence of a metal addition catalyst.

U.S. Pat. No. 4,496,474 discloses the reaction of 2-pentenenitrile and alkylamines to produce the corresponding nitrile compound.

SUMMARY OF THE INVENTION

The present invention is an improved process for the production of alkylaminonitriles. It has now been found that the reaction proceeds at a faster rate and more selectively if the reaction mixture contains between about 15 and 60% by weight water. The molar concentration of the 2-pentenenitrile to alkylamine is preferably in the range of about 0.3 to 3. The reaction mixture is reacted at a temperature in the range of about 20° C. to 200° C. at a pressure in the range of about atmospheric to about 10 atmospheres. No catalyst is required.

Suitable alkylamines for use in the process include methylamine, dimethylamine, dodecylamine, ethylenediamine, 2-methylpentamethylenediamine, 1,3-diaminopentane, 1,2-diaminocyclohexane, 3-methylpiperidine, hexamethylenediamine, octadecylamine, and piperazine. Typically the alkylamines useful in the invention have between 1 and 10 carbon atoms.

Some reaction products of the cyanobutylation have the formula:

$$CH_3CH_2CHCH_2CN \text{ and } CNCH_2CHNHR_2NHCHCH_2CN$$
$$\underset{NHR_1}{|} \qquad \underset{C_2H_5}{|} \qquad \underset{C_2H_5}{|}$$

where $R_1$ and $R_2$ each typically have 1 to 10 carbon atoms and are selected from the group consisting of alkyl, alkaline alkylamino, cycloalkyl.

Also some reaction products have the formula:

$$NCCH_2CH-N\underset{C_2H_5}{\overset{}{|}}\diagup\hspace{-0.3em}\diagdown N-CHCH_2CN\underset{C_2H_5}{\overset{}{|}}$$

These reaction products may be hydrogenated over suitable catalysts to form 1,3-pentanediamines which are useful as monomers for polyamides and isocyanates, and as chain extenders and epoxy curing agents. Suitable catalysts include: Raney nickel, Raney cobalt, palladium, platinum, ruthenium, iron, supported cobalt and nickel. Suitable catalyst supports include: alumina, carbon, silica, kieselguhr. Suitable hydrogenation temperatures are about 75° C. to 150° C. Suitable pressures are about 500 psig to 3000 psig. The mixture to be hydrogenated may contain ammonia, caustic, water or a combination of these. Solvents such as alcohols and ethers such as methanol and tetrahydrofuran, dioxane, butanol, isopropanol, may be employed as necessary or desired.

DETAILED DESCRIPTION OF THE INVENTION

The cyanobutylation reactions can be run from 20° C. to 200° C., preferably 50° C. to 80° C., either at atmospheric or autogeneous pressure. It is possible to employ superatmospheric pressure, for example up to 10 atmospheres. Water should be present in the amounts of 15 to 60% by weight of the reaction mixture, and 25 to 40% by weight is preferred.

The molar ratio of 2-pentenenitrile to amine should be 0.3 to 3 moles per mole of amine. Excess of 2-pentenenitrile over the stoichiometric amount is required when one wants to make the dinitrile from the starting diamine. Typically a 10 to 15% mole excess is employed. Either the cis- or trans- 2-pentenenitrile may be employed for the cyanobutylation process. Mixtures of the two isomers may also be used.

Although the cyanobutylation reaction is carried out in general in the absence of solvents, it is possible to use organic solvents which are inert under the reaction conditions. Suitable solvents include dioxane, tetrahydrofuran, dimethylformamide, dimethylacetamide, methanol, butanol, isopropanol.

The reaction may be carried out batchwise or continuously, using water which is homogeneously dissolved or suspended in the liquid phase.

In the batchwise case, the cyanobutylation is carried out, for example, by stirring a mixture of 2-pentenenitrile, water and amine at the stated temperature and pressure until the conversion is as complete as possible. The reaction mixture is then distilled to obtain the desired alkylaminonitriles.

EXAMPLES

Example 1

Cyanobutylation of Aqueous Ethylenediamine with cis-2-pentenenitrile

A solution of 78 g (1.3 moles) ethylenediamine in 117 g water (40 wt % ethylenediamine in water) was added in one portion to 120 g (99%, 1.47 moles) cis-2-pentenenitrile followed by heating the mixture to 75° C. After 20 minutes the mixture became homogeneous and contained, by gas chromatography analysis, both the 1:1 and 2:1 adducts respectively in a 2:1 ratio. The conversion of cis-2-pentenenitrile was 99%. The yield of the 1:1 adduct, 3-N-(2-aminoethylamino)pentanentrile, and the 2:1 adduct, bis(N,N'-2-cyanoethyl-1-ethyl)ethylenediamine, was 56.2% and 39.8%, respectively from converted cis-2-pentenenitrile. Small concentrations of trans-2-pentenenitrile (0.074 wt. %) and 3PN (0.32 wt %) by-products were also observed in the product mixture.

Example 2

Comparison of Cyanobutylation of Anhydrous Ethylenediamine and cis-2-Pentenenitrile and Aqueous Ethylenediamine A mixture of 120 g (99%, 1.47 moles) (cis-2-pentenenitrile) and 78 g (1.3 moles) ethylenediamine was heated at 75° C. and sampled periodically. A comparison of cis-2-pentenenitrile conversion and 1:1 and 2:1 product yields for this run vs those containing 10% and 37% water is summarized below:

|  | (60 min) | (60 min) | (20 min) |
|---|---|---|---|
| % cis-2-pentenenitrile Conv. | 56.3 | 76.7 | 99 |
| % Water By Weight | 0 | 10 | 37 |
|  | | % Yield | |
| % 1:1 Adduct | 19.5 | 60.2 | 56.2 |
| % 2:1 Adduct | 0 | 10.7 | 39.8 |
| % trans-2-pentenenitrile | 41.3 | 16.9 | <1 |
| % 3-pentenenitrile | 34.3 | 9.0 | <1 |
| % 4-pentenenitrile | 4.9 | 2.3 | n.d. |

This comparison shows the effect of water concentration on accelerating the reaction rate and product selectivity vs its absence. Note that the conversion of cis-2-pentenenitrile was 99% after 60 minutes employing 37% water vs 56% and 77% after 60 minutes for 0% and 10% water, respectively.

Example 3

Cyanobutylation using Excess Aqueous Ethylenediamine and cis-2-Pentenenitrile

A mixture of 120 g (99%, 1.47 moles) cis-2-pentenenitrile and 144 g (2.4 moles) ethylenediamine in 144 g water (40% ethylenediamine) was stirred and heated at 75° C. for 15 minutes. Conversion of cis-2-pentenenitrile was 99% and the ratio of 1:1 to 2:1 adduct was 5:1. The yields of the 1:1 and 2:1 adducts from cis-2-pentenenitrile were 77.3% and 18.9%, respectively. The combined yield of trans-2-pentenenitrile, 3-pentenenitrile and 4-pentenenitrile by-products was 1%.

Example 4

Cyanobutylation using Aqueous Ethylenediamine and Excess cis-2-Pentenenitrile

A mixture of 150 g (99%, 1.83 moles) cis-2-pentenenitrile and 36 g (0.60 mole) ethylenediamine in 54 g water was heated and stirred at 75° C. for 5 hours. Two phases were produced. The top organic product contained unreacted cis-2-pentenenitrile and a mixture of both the 2:1 and 1:1 adducts in a ratio of 64:1. The yield of the 2:1 adduct based on consumed EDA was 67.4%.

Example 5

Cyanobutylation of Aqueous Ethylenediamine with trans-2-Pentenenitrile

A mixture of 25 g (0.309 mole) trans-2-pentenenitrile and 30 g (0.500 mole) ethylenediamine in 45 g water was vigorously mixed at 75° C. for 60 minutes. A sample taken after 15 minutes showed 99% conversion of trans-2-pentenenitrile to the 1:1 adduct in 75.7% yield. The yield of the 2:1 adduct was 21%. The conversion and yields are similar to that for cis-2-pentenenitrile described in Example 3 above.

Example 6

Cyanobutylation of Aqueous 2-Methylpentamethylenediamine with cis-2-Pentenenitrile A mixture of 76 g (0.938 mole) cis-2-pentenenitrile and 114 g (1.0 mole) 2-methylpentamethylenediamine in 171 g water was vigorously stirred at 55° C. for 90 minutes to yield a homogeneous solution. Gas chromatographic analysis of the solution showed a 99% conversion of cis-2-pentenenitrile to the 1:1 and 2:1 adducts. Because of the dissymmetry of the 2-methylpentamethylenediamine, two 1:1 adducts were observed with methylpentamethylenediamine, in a 66/37 molar ratio. The major 1:1 adduct was 3-(5-amino-4-methylpentylamino)pentanenitrile and the minor, 3-(5-amino-3-methylpentylamino)pentanenitrile. The yield of the 1:1 aminonitrile combined adducts was 72%. A 14.6% yield of the 2:1 adduct was also observed.

Example 7

Cyanobutylation of Aqueous 3-Methylpiperidine with cis-2-Pentenenitrile

A mixture of 38 g (0.469 mole) (cis-2-pentenenitrile) and 53.5 g (0.540 mole) 3-methylpiperidine in 80.5 g water was vigorously stirred at 95° C. for 9 hours. Two layers were observed and separated. The organic layer was analyzed by gas chromatography and showed 97.7% conversion of cis-2-pentenenitrile. The yield of the 1:1 adduct, 3-(3-methylpiperidyl)pentanenitrile, was 95%. A 5% yield of combined trans-2-pentenenitrile and 3-pentenenitrile were produced. Two isomeric aminonitrile adducts were observed both having a m/e of 180 (molecular weight ion) by GC/MS analysis.

Example 8

Cyanobutylation of N-Dodecylamine with cis-2-Pentenenitrile. Comparison with and without water.

A mixture of 38 g (0.469 mole) cis-2-pentenenitrile, 74 g (0.400 mole) N-dodecylamine and 40 g water was vigorously stirred and heated at 110° C. in a 300 mL stainless steel autoclave at autogeneous pressure for 5 hours. Analysis by gas chromatography of the organic layer indicated a 59% conversion of N-dodecylamine to the aminonitrile, 3-(dodecylamino)pentanenitrile, in 98% yield. The excess cis-2-pentenenitrile was converted to a mixture of 22.8% 3-pentenenitrile and trans-2-pentenenitrile.

A similar reaction was run under the same reaction conditions, but without water. In this case the initial mix was homogeneous. After 5 hours, the conversion of N-dodecylamine was only 12.2%. The yield of 3-(dodecylamino)pentanenitrile was 81.8% based on converted N-dodecylamine. The excess cis-2-pentenenitrile was converted to 3-pentenenitrile and trans-2-pentenenitrile in 38% yield.

Example 9

Cyanobutylation of Piperazine with cis-2-Pentenenitrile

A solution of 182 g (80.6 g piperazine equivalent, 0.938 mole) piperazine hexahydrate in 100 g water was mixed vigorously with 38 g (0.469 mole, 99%) cis-2-pentenenitrile at 65° C. for 60 minutes. The initial heterogeneous mixture became homogeneous after 5 minutes. Analysis by gas chromatography of the solution after 5 minutes showed complete conversion of cis-2-pentenenitrile to 3-(piperazinyl)pentanenitrile in 99% yield. No trans-2-pentenenitrile or 3-pentenenitrile were detected. Upon standing at 25° C. for 3 days, a white crystalline solid precipitated. Infrared and mass spectral analysis indicated the product to be the 2:1 adduct of cis-2-pentenenitrile and piperizine: i.e., the

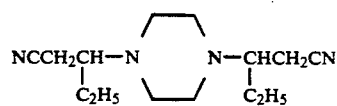

Example 10

Cyanobutylation of Aqueous Methylamine with cis-2-Pentenenitrile

A mixture of 356 g (99%, 4.35 moles) cis-2-pentenenitrile and 400 g of 40% aqueous methylamine was stirred vigorously at 40° C. for one hour during which time the temperature rose to 78° C. The initially heterogeneous mixture became homogeneous after one hour. GC analysis of the solution indicated a 99% cis-2-pentenenitrile conversion and a 98% yield of 3-(methylamino)pentanenitrile.

Example 11

Cyanobutylation of Aqueous Dimethylamine and cis-2-Pentenenitrile

Aqueous 40% dimethylamine (580 g) was added dropwise to 356 g (99%, 4.35 moles) cis-2-pentenenitrile at 25° C. After the addition, the temperature rose to 60° and the reaction continued for one hour. The two layers were separated. GC analysis of the organic and aqueous layers showed concentrations of 91 wt % and 21 wt %, respectively for the product 3-(N,N-dimethylamino)-pentanenitrile. The yield of the aminonitrile was 99% at a 99% cis-2-pentenenitrile conversion.

Example 12

Cyanobutylation of Aqueous Octadecylamine with c-2PN

Into a 100 mL three-necked round-bottomed flask equipped with a mechanical stirrer, thermometer and condenser was charged 2.7 g (99%, 0.0336 mole) cis-2-pentenenitrile, 10 g (0.0372 mole) octadecylamine and 4.25 g water (25 wt %). The mixture was vigorously stirred at 80° C. for 6 hours followed by cooling to 40° C. To this mixture was added 25 g methanol to produce a clear homogeneous solution. A sample was removed and analyzed. Analysis indicated a 65% cis-2-pentenenitrile conversion and a 84.5% yield of the aminonitrile, 3-octadecylaminopentanenitrile. After standing overnight, a waxy white solid of the aminonitrile was observed and filtered to yield 12 g of 87% pure product.

The reaction was run in a similar fashion with the exception that varying amounts of water and/or methanol were employed. The results shown below indicate a higher cis-2-pentenenitrile conversion and aminonitrile yield with higher water concentration. Methanol appears not to have an effect on aminonitrile yield. No precipitate of the aminonitrile was observed where low concentrations of water and/or methanol was employed.

| Wt % H$_2$O | Wt % CH$_3$OH | cis-2-pentenenitrile Conv. | % Yield Aminonitrile |
|---|---|---|---|
| 25 | 0 | 65.0 | 84.5 |
| 5.2 | 0 | 44.3 | 29.6 |
| 25 | 5.0 | 88.1 | 76.3 |
| 5.2 | 5.0 | 73.0 | 18.2 |
| 0 | 5.2 | 46.5 | 18.0 |

I claim:

1. A process for the cyanobutylation of amines with 2-pentenenitrile which comprises forming a reaction mixture of an amine selected from the class consisting of alkylamines having 1 to 10 carbon atoms, dimethylamine, dodecylamine, ethylenediamine, 2-methylpentamethylenediamine, 1,3-diaminopentane, 1,2-diaminocyclohexane, 3-methylpiperidine, octadecylamine hexamethylenediamine, and piperazine; 2-pentenenitrile and water, in which the molar ratio of 2-pentenenitrile to amine is 0.3 to 3, and the water concentration is between 15 and 60% by weight of the reaction mixture, and reacting the mixture at a temperature in the range of about 20 degrees to 200 degrees C. at a pressure in the range of about atmospheric to about 10 atmospheres.

2. The process of claim 1 in which the 2-pentenenitrile is the cis isomer.

3. The process of claim 2 in which the reaction is carried out in the absence of catalyst.

4. The process of claim 1 in which the process is carried out in the presence of a solvent.

5. The process of claim 1 in which the 2-pentenenitrile is the trans isomer.

6. The process of claim 1 in which the reaction products have the formula:

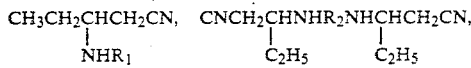

and

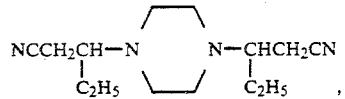

where R$_1$ is alkyl or alkylamino, and R$_2$ is alkylene.